United States Patent
Baek et al.

(10) Patent No.: US 9,017,638 B2
(45) Date of Patent: Apr. 28, 2015

(54) GRAPHENE PREPARED BY USING EDGE FUNCTIONALIZATION OF GRAPHITE

(75) Inventors: Jong Beom Baek, Ulsan (KR); Eun Kyoung Choi, Chungbuk (KR); In Yup Jeon, Chungbuk (KR); Seo Yun Bae, Gyeonggi-do (KR)

(73) Assignee: Unist Academy-Industry Research Corp (KR)

( * ) Notice: Subject to any disclaimer, the term of this patent is extended or adjusted under 35 U.S.C. 154(b) by 269 days.

(21) Appl. No.: 13/404,918

(22) Filed: Feb. 24, 2012

(65) Prior Publication Data

US 2013/0108540 A1   May 2, 2013

(30) Foreign Application Priority Data

Oct. 26, 2011 (KR) .......................... 10-2011-0110319

(51) Int. Cl.
| | | |
|---|---|---|
| C01B 31/02 | (2006.01) | |
| C07C 221/00 | (2006.01) | |
| C07C 45/00 | (2006.01) | |
| B82B 3/00 | (2006.01) | |
| B82B 1/00 | (2006.01) | |
| C01B 31/04 | (2006.01) | |
| C01B 3/00 | (2006.01) | |
| B82Y 40/00 | (2011.01) | |
| B82Y 30/00 | (2011.01) | |

(52) U.S. Cl.
CPC .......... *C01B 31/0469* (2013.01); *C07C 221/00* (2013.01); *C01B 3/0021* (2013.01); *Y02E 60/325* (2013.01); *B82Y 40/00* (2013.01); *B82Y 30/00* (2013.01); *Y10S 977/734* (2013.01); *Y10S 977/847* (2013.01)

(58) Field of Classification Search
CPC ....................................................... C01B 31/04
USPC ........... 423/448; 564/394; 568/322; 977/734, 977/847
See application file for complete search history.

(56) References Cited

U.S. PATENT DOCUMENTS

2007/0041887 A1* 2/2007 Veedu et al. ................ 423/447.2

FOREIGN PATENT DOCUMENTS

WO   WO 2010/096665   *   8/2010 ................ D01F 9/00

OTHER PUBLICATIONS

Charlier, et al., Graphite Interplanar Bonding: Electronic Delocalization and van der Waals Interaction, Europhysics Letters 1994; 28(6): 403-408.*

(Continued)

*Primary Examiner* — Daniel C McCracken
(74) *Attorney, Agent, or Firm* — Amy Allen Hinson; John B. Hardaway, III; Nexsen Pruet, LLC

(57) ABSTRACT

Disclosed is a method for producing graphene functionalized at its edge positions of graphite. Organic material having one or more functional groups is reacted with graphite in reaction medium comprising methanesulfonic acid and phosphorus pentoxide, or in reaction medium comprising trifluoromethanesulfonic acid, to produce graphene having organic material fuctionalized at edges. And then, high purity and large scaled graphene and film can be obtained by dispersing, centrifugal separating the functionalized graphene in a solvent and reducing, in particular heat treating the graphene. According to the present invention graphene can be produced inexpensively in a large amount with a minimum loss of graphite. (FIG. 1)

11 Claims, 2 Drawing Sheets

(56) References Cited

OTHER PUBLICATIONS

K.S. Novoselov, et al. "Electric Field Effect in Atomically Thin Carbon Films." Science 206, 666 (2004); DOI: 10.1126/science. 1102896. pp. 666-669.

Keun Soo Kim, et at. "Large-scale pattern growth of graphene films for stretchable transparent electrodes." vol. 457|5 Feb. 2009| doi:10. 1038/nature07719. pp. 706-710.

Sasha Stankovich, et al. "Synthesis of graphene-based nanosheets via chemical reduction of exfoliated graphite oxide."Science Direct, Carbon 45 (2007) 1558-1565.

\* cited by examiner

GRAPHENE PREPARED BY USING EDGE FUNCTIONALIZATION OF GRAPHITE

CROSS REFERENCE TO RELATED APPLICATION

This application claims priority to Korean Application No. KR10-2011-0110139 filed Oct. 26, 2011.

FIELD OF THE INVENTION

This invention relates to a method tor preparing graphene by functionalizing edge positions of graphite, and in particular to an edge functionalized graphene, produced by reacting organic material and graphite in the presence of a reaction medium comprising methanesulfonic acid and phosphorus pentoxide or a reaction medium comprising trifluoromethanesulfonic acid and to a method for preparing the same.

BACKGROUND OF THE INVENTION

Generally, graphite is a material having a typical layered, planar structure where two-dimensional graphene sheets stack. In each layer, carbon atoms are arranged in a hexagonal lattice. Graphene is a typical single layer sheet in which three carbon atoms are bonded together by $sp^2$ hybrid orbital bonds arranged in a hexagonal crystal lattice.

In graphite, the bond between carbon atoms within one layer of graphite, i.e., graphene, is a strong covalent bond, but, the one between adjacent graphene layers is the Van der Waals bond, which is extremely weak compared to the covalent bond.

Graphene is one layer of graphite, i.e., a single layer of graphite. In graphite as the bond between adjacent graphene layers is very weak as described above, there can exist graphene which has a very thin two-dimensional structure of a thickness of about 4Å.

Graphene has unusual properties different from common materials. The most noticeable property found in graphene is that electrons flow like zero mass where electrons transfer in graphene. Thus electrons flow with the same velocity as light transfers i.e., with a velocity of light in vacuum. In addition, graphene shows the feature of a half-integer quantum hall effect, abnormal relative to electron and hole.

Also, currently known electron mobility of graphene has a high value of about 20,000 to 50,000 $cm^2/Vs$. For example, carbon nanotubes are in a family similar to graphene since carbon nanotubes have very low yield where they are subject to refining after synthesis even when the synthesis is made using inexpensive material and their final product is expensive. Meanwhile graphene has a benefit of very inexpensive cost. Also, in the case of single walled carbon nanotubes, according to their chiral property and diameter, metal and semiconductor features vary and even if they have the same semiconductor feature, they have bandgaps that are all different. Thus to utilize a specific semiconductor property or metal property from a given single walled carbon nanotube, single walled carbon nanotubes each should be separated. However, it is known that this is very hard.

On the other hand, in the case of graphene, since its electrical property varies according to crystal directionality of graphene of a given thickness, a user can exhibit an electrical property into its selected direction and thus graphene has the merit that the user can easily design a device. Such features of graphene are very effectively available in carbon based electrical devices or carbon based electromagnetic devices.

Graphene has thus attracted much attention due to its useful and unusual properties as a substituent material for the next generation silicon and indium tin oxide.

Therefore, various methods for obtaining graphene have been continuously reported since 2004 and the methods generally includes mechanical exfoliation, chemical exfoliation, SiC crystal grown by thermal decomposition, exfoliation-reintercalation-expansion method, chemical vapor deposition and epitaxial synthesis, etc.

A mechanical exfoliation method utilizes the adhesive force of scotch tape, which comprises first attaching a cellophane tape to a graphite sample and detaching the cellophane tape from the graphite sample and then collecting graphene exfoliated from the graphite and attached on the surface of the cellophane tape. However, in the case of this mechanical exfoliation, the exfoliated graphene has the shape of torn paper and is thus not uniform. Further the size of the graphene is a mere level of micrometer and it is impossible to obtain a large size of graphene. As the final yield is extremely low, there is a problem that many samples are not suitable for necessary researches.

A chemical exfoliation method involves oxidizing graphite and crushing the graphite oxide via ultrasonic waves, etc., to prepare graphene oxide dispersed in an aqueous solution and then again reducing the graphene oxide by a reducing agent such as hydrazine to graphene. However, the graphene oxide is not completely reduced and only about 70% of graphene oxide is reduced, thus there still remains many defects in the graphene. Therefore, there is the problem that good physical and electrical properties specific to graphene get lowered.

A SiC crystal thermal decomposition method involves the principle that SiC is decomposed at its surface when a SiC single crystal is heated and then Si is removed and graphene is generated by the remaining Carbons. However, in the case of this thermal decomposition method, a SiC single crystal, which is used as a starting material, is extremely expensive and it is very hard to obtain large-scaled graphene.

An exfoliation-reintercalation-expanson method involves inserting fuming sulfuric acid into graphite, placing the resultant graphite on a furnace of high temperature and thus the sulfuric acid is expanded and at the same time the graphite is expanded by the gas, and dispersing, the graphite in a surfactant such as TBA to produce graphene. The exfoliation-reintercalation-expansion method also has a low yield of graphene and does not exhibit satisfactory electric properties due to a high interlayer resistance according to the surfactant.

A chemical vapor deposition method involves using transition metals, which easily form a carbon and carbide alloy or properly adsorb carbon at high temperature, as a catalytic layer to synthesize graphene. This method is a complicated process, uses a heavy metal catalyst and entails many limitations for mass production.

An epitaxial synthesis method utilizes a principle that carbon adsorbed on and included in the crystal is growing into graphene along the texture of the substrate surface at high temperature. Graphene manufactured by this synthesis method is very expensive and it is terribly difficult to fabricate a device, as well as it has a lower electric property than that grown by the mechanical exfoliation and chemical vapor deposition methods.

In particular, regarding the method for producing graphene using the above chemical vapor deposition, there is Korea Patent No. 923304 entitled "Graphene Sheets and Method of Producing the Same". This Patent proposed a method for optimizing a chemical vapor deposition process among Graphene Production Methods. However, as this method uses a catalyst (a catalyst for graphitization), it entails a process for removing the catalyst by acid treatment and a complicated process for producing graphene.

Also, disclosed is U.S. Patent Application Pub. No. 2010/0047154 A1 entitled "Method for preparing graphene ribbons" which is a method for mass production of ribbons comprising: cutting graphite into a short form and permeating water into the crumbled graphite and freezing and expanding the water containing graphite. This description describes a method for production of graphene where graphite is physically cut and graphene is produced using a tensile stress due to a volume expansion while water is frozen. Ultrasonic wave treatment and hydrophilic treatment are required. There is a limitation that not graphene sheets but simply graphene pieces in ribbon forms are obtainable.

SUMMARY OF THE INVENTION

To solve many problems in convenient methods for fabricating graphene, shown above, this invention has an object of providing graphene edges of which are functionalized, fabricated by reacting organic material and graphite in the presence of a reaction medium including methanesulfonic acid and phosphorus pentoxide or of trifluoromethanesulfonic acid, a method of fabricating the same, and graphene obtained by the method.

As shown above, the object of this invention is accomplished by a method of fabricating graphene edges of which are functionalized, reacting organic material having the functional group and graphite in reaction medium comprising methanesulfonic acid and phosphorus pentoxide, or in reaction medium comprising trifluoromethanesulfonic acid, substituting bonds at edges between graphenes with covalent bonds between graphene and organic material where the functional group includes at least one group selected from the group consisting of carboxylic acid group, amide group, sulfonic acid group, carbonyl chloride group and carbonyl bromide group. In addition, in this invention the reaction medium which comprises methanesulfonic acid and phosphorus pentoxide includes methanesulfonic acid 65 wt % to 95 wt % and phosphorus pentoxide 5 wt % to 35 wt % based on the total weight of the reaction medium.

Preferably, organic material bonded to the graphene acts as a wedge, and thereby graphene edges of which are functionalized are exfoliated.

In addition, the organic material is preferably to be benzoic acid unsubstituted or substituted by one or more substituents selected from the group consisting of halo, nitro, amino, cyano, mercapto, hydroxyl, C1-C4 alkyl, C1-C4 alkoxy, formyl, C1-C4 alkylcarbonyl, phenyl, benzoyl, carbonyl and the combination thereof.

Also, the organic material is any one of the compounds selected from the group consisting of 3-aminobenzoic acid, 4-aminobenzoic acid, 4-(4-aminophenyl)benzoic acid, 4-(3-aminophenyl)benzoic acid, 5-aminoisophthalic acid, 4-(4-aminophenoxy)benzoic acid, 4-(3-aminophenoxy)benzoic acid, 3,4-diaminobenzoic acid, 3,5-diaminobenzoic acid, 2-phenoxybenzoic acid, 3-phenoxybenzoic acid, 4-phenoxybenzoic acid, 3,5-diphenoxybenzoic acid, 5-phenoxyisophthalic acid, 4-phenyl-(4-phenoxy benzoic acid), 4-phenoxy-(4-phenylbenzoic acid), 4-ethylbenzoic acid, 2-ethylbenzoic acid and 4-ethylphenoxybenzoic acid.

And, in this invention is provided a method for fabricating graphene functionalized at its edges comprising a step of dispersing graphene functionalized at its edges in solvent, centrifugally separating the graphene and separating the graphene from graphite.

And, in this invention is provided a method for fabricating graphene comprising a step of reducing graphene functionalized at its edges in air or in an inert atmosphere, and removing organic material which functionalized the edges of the graphene.

The reduction is a heat treatment performing at temperatures of 300° C. to 1,200° C. for 30 minutes to 24 hours. The graphene obtained after removing the organic material has a purity that is from 90% to 99%, and comprises one layer or a plurality of layers and has a thickness that is from 0.3 nm to 1000 nm.

According to this invention, edges of each graphene forming graphite can be functionalized with organic material having various functional groups, by the reaction of the organic material having various functional groups with graphite in reaction medium comprising methanesulfonic acid and phosphorus pentoxide, or in reaction medium comprising trifluoromethanesulfonic acid.

The organic material acts as a wedge and thus graphene having functional groups at its edges is easy to obtain. And through an additional treatment (separation of graphene having functional groups at its edges and removal of functionalizing organic material) the graphene having functional groups at its edges of high purity can be easily obtained.

In addition, because the functionalization of edge positions of each graphene forming graphite with organic material is performed under milder conditions under the present invention, i.e., in reaction medium comprising methanesulfonic acid and phosphorus pentoxide, or in reaction medium comprising trifluoromethanesulfonic acid, than methods of fabricating graphene in the prior art, loss of graphite and graphene can be minimized.

As this invention provides the advantages of both mass production of chemical exfoliation and of production of a high level of purity of graphene, production of a high purity graphene at a low cost as well as through mass production is possible.

Accordingly, this invention enlarges the potential of graphene applications and the material thus obtained finds a wide use in various applications such as next generation silicons, semiconductors, wafers for solar cells, ITO(indium tin oxide) transparent electrodes, hydrogen storage materials, optical fibers, and electronic devices.

DETAILED DESCRIPTION OF THE INVENTION AND PREFERRED EMBODIMENTS

Figure 1:
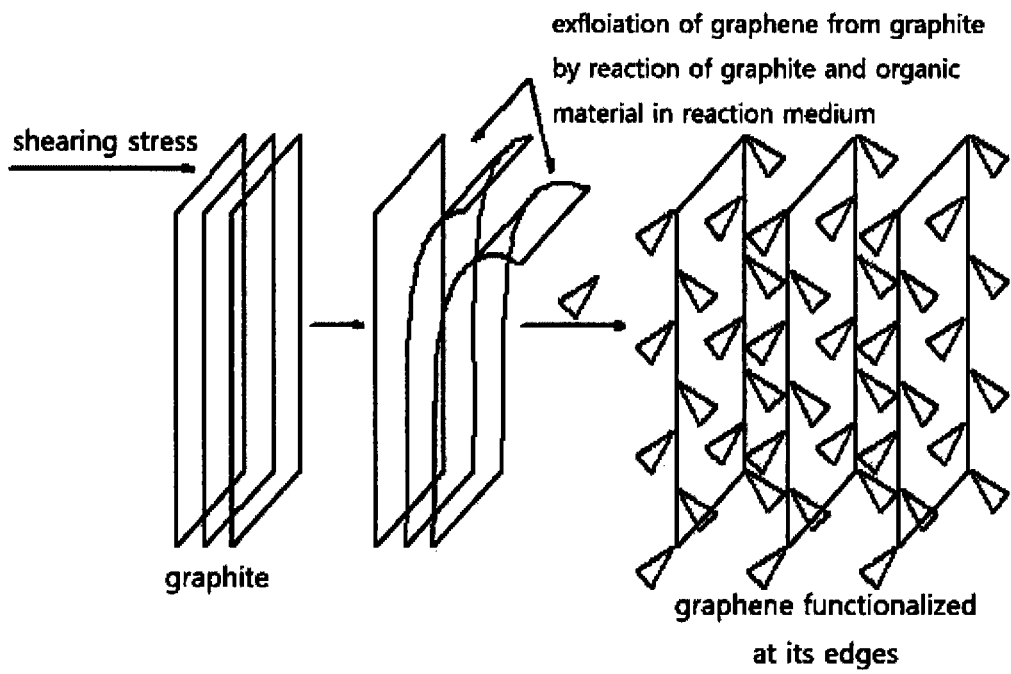
FIG. 1 shows schematically a production process of graphene via the functionalization of graphite according to the present invention.

The invention is directed to a method of producing graphene, which is a high functional carbon material. The method produces graphene in a simple way, at low cost, and through mass production, The invention is also directed to the graphene thus obtained.

The present invention relates to a process for producing graphene functionalized at its edges by reacting graphite and organic material, a method for obtaining graphene by removing organic material on the graphene functionalized at its edge positions, and graphene obtained according to the above. The present invention will now be described in detail as follows:

Graphene functionalized at its edges according to the present invention is produced by a method comprising: reacting organic material having one or more functional groups with graphite in a reaction medium comprising methanesulfonic acid and phosphorus pentoxide, or in a reaction medium comprising trifluoromethanesulfonic acid, thus to substitute bonds of edge positions between the graphene forming the graphite with covalent bonds between the graphene and organic material.

The one or more functional groups include one or more groups selected from a group consisting of a carboxylic acid group, amide group, sulfonic acid group, carbonyl chloride group and carbonyl bromide group. The polymeric phosphoric acid is a weak acid.

Since the phosphorus pentoxide reacts with water, it changes into polymeric phosphoric acid. The phosphorus pentoxide does not have other effects on the reaction except the promotion of the reaction of both graphite and organic material. In addition, as the phosphorus pentoxide easily dissolves in water, it is easy to remove.

The methanesulfonic acid is a strong acid. The phosphoric acid has a pH value of −3 to 1, and preferably of −2 to −1.

The methanesulfonic acid acts as a strong acid and also has little effect on the original structure of graphite. Thus, the methanesulfonic acid has an advantage that it does not weaken the original structure of graphite. Also, as the methanesulfonic acid dissolves in water, it is also easily removable.

It is preferable that the reaction medium, which contains methanesulfonic acid and phosphorus pentoxide, comprises 65 wt % to 95 wt % of methanesulfonic acid and 5 wt % to 35 wt % of phosphorus pentoxide based on the total weight of the reaction medium.

The functional group which the organic material has is one or more groups selected from a group consisting of a carboxylic acid group, amide group, sulfonic acid group, carbonyl chloride group and carbonyl bromide group.

Preferably, the functional group of the organic material is one or more groups selected from the group consisting of —COOH, —CONH$_2$, —CONR'H, —CONR'R", —SO$_3$H, —COCl and —COBr, wherein R' and R" are each independently C$_1$-C$_5$ alkyl group. C$_6$-C$_{10}$ aryl group, or C$_6$-C$_{10}$ aralkyl group, and the alkyl group, aryl group, or aralkyl group is unsubstituted or substituted by the substituent selected from the group consisting of a halo, nitro, amino, cyano, mercapto, hydroxyl, C$_1$-C$_4$ alkyl, C$_1$-C$_4$ alkoxy, formyl, C$_1$-C$_4$ alkylcarbonyl, phenyl, benzoyl, phenoxy and combinations thereof.

The organic material comprises one or more functional groups. The remaining portion thereof except the one or more functional groups includes C$_1$-C$_5$ alkyl group, C$_2$-C$_5$ alkenyl group, C$_2$-C$_5$ alkynyl group, C$_3$-C$_{10}$ cycloalkyl group, C$_6$-C$_{15}$ aryl group, or C$_6$-C$_{15}$ aralkyl group, and the alkyl group, alkenyl group, alkynyl group, cycloalkyl group, aryl group, or aralkyl group and is unsubstituted or substituted by the substituent selected from the group consisting of halo, nitro, amino, cyano, mercapto, hydroxyl, C$_1$-C$_4$ alkyl, C$_1$-C$_4$ alkoxy, formyl, C$_1$-C$_4$ alkylcarbonyl, phenyl, benzoyl, phenoxy and combinations thereof.

The organic material is, preferably, a benzoic acid which is unsubstituted or substituted, wherein the substituents are selected from the group consisting of a halo, nitro, amino, cyano, mercapto, hydroxyl, C$_1$-C$_4$ alkyl, C$_1$-C$_4$ alkoxy, formyl, C$_1$-C$_4$ alkylcarbonyl, phenyl, benzoyl and mixtures thereof.

More preferably, the organic material is any one of the compounds selected from 3-aminobenzoic acid, 4-aminobenzoic acid, 4-(4-aminophenyl)benzoic acid, 4-(3-aminophenyl)benzoic acid, 5-aminoisophthalic acid, 4-(4-aminophenoxy)benzoic acid, 4-(3-aminophenoxy)benzoic acid, 3,4-diaminobenzoic acid, 3,5-diaminobenzoic acid, 2-phenoxybenzoic acid, 3-phenoxybenzoic acid, 4-phenoxybenzoic acid, 3,5-diphenoxybenzoic acid, 5-phenoxyisophthalic acid, 4-phenyl-(4-phenoxy benzoic acid), 4-phenoxy-(4-phenylbenzoic acid), 4-ethylbenzoic acid, 2-ethylbenzoic acid and 4-ethylphenoxybenzoic acid.

The organic material and graphite are reacted in the presence of a reaction medium comprising methanesulfonic acid and phosphorus pentoxide or a reaction medium comprising trifluoromethanesulfonic acid. The weight ratio of the organic material to graphite during the reaction being in the range of from 2:1 to 1:5, and preferably in the range of 3:2 to 1:3.

At this time, the reaction temperature is 100 to 160° C., preferably 120 to 140° C. At a reaction temperature of less than 100° C., there is a problem that a reaction does not occur; while at a reaction temperature of more than 160° C., there is a problem that a side reaction greatly occurs.

The reaction time is 12 hours to 120 hours, and preferably 60 hours to 84 hours. When the reaction time is less than 12 hours, the reaction is not completed. When the reaction time is more than 120 hours, the reaction is not any more progressed.

The reaction is performed with 0.01 to 40 weight part of graphite, relative to 100 weight part of the reaction medium.

Through the reaction between the organic material and graphite, graphene functionalized at its edge positions by organic material is produced.

That is, graphite and organic material are reacted in the reaction, thus bonds of edge positions between the graphene, each of which is each layer of graphite, are substituted by the covalent bonds of the functional groups and carbons at the edges of the graphene. In this manner, the organic material combined with the graphene forming graphite acts as a wedge to exfoliate the graphene from the graphite.

FIG. 1 shows one example of the reaction according to the present invention, which schematically shows that organic material having functional group(s) and graphite are reacted in a reaction medium comprising methanesulfonic acid and phosphorus pentoxide or a reaction medium comprising trifluoromethanesulfonic acid to functionalize the edges of the graphene, i.e., each layer of graphite by organic material so that the organic material thus functionalized acts as a wedge and exfoliation of graphene thus occurs.

Figure 2:
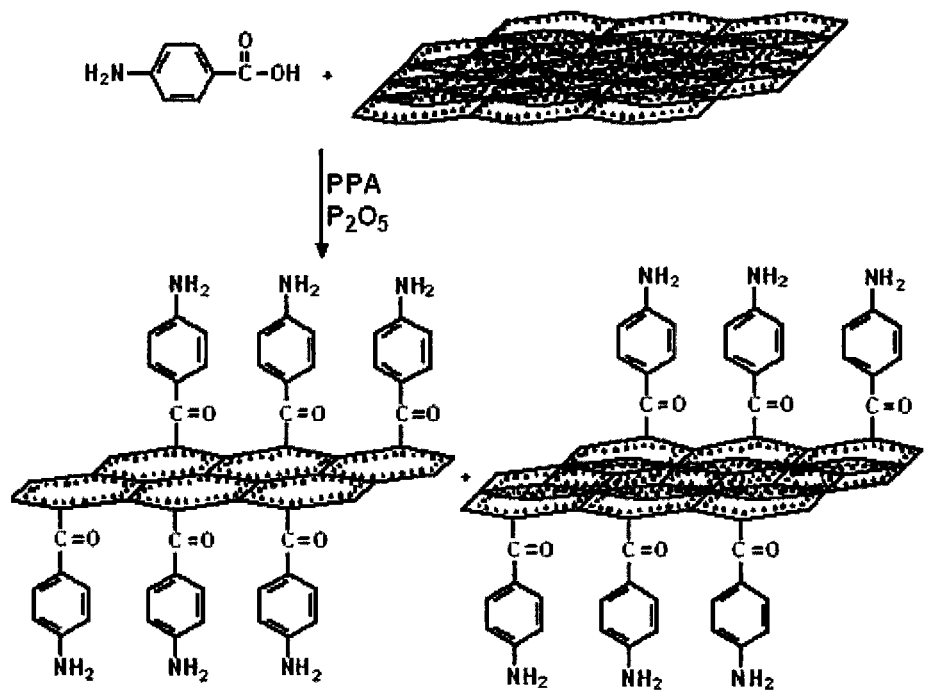
FIG. 2 shows a production process of graphene according to one example of the present invention.

FIG. 2 more specifically shows one example of the reaction according to the present invention, which shows the reaction according to the present invention in which p-aminobenzoic acid is used as organic material having functionalized group (s) in a reaction medium comprising methanesulfonic acid and phosphorus pentoxide or reaction medium comprising trifluoromethanesulfonic acid.

If the organic material and the graphite are reacted in the reaction medium comprising polymeric phosphoric acid and phosphorus pentoxide, the graphene functionalized at the edges as described above is formed. Among the reaction products, graphite and organic matter not reacted, except the graphene functionalized at the edges, coexist with polymeric phosphoric acid and phosphorus pentoxide.

So as to remove methanesulfonic acid and phosphorus pentoxide or trifluoromethanesulfonic acid, and the organic material from the reaction products of various compounds which coexist with each other, the reaction products are subject to washing by water and then to washing by alcohol such as methanol. And then the washed products can be dried using a method such as a freeze drying.

If freeze drying is carried out, drying is achieved in the spaces between the generated graphene which have edge positions functionalized and being held as their spaces are. Thus, when freeze dried products obtained through such freeze drying are again dissolved in solvent, the solvent can easily permeate the spaces between the functionalized graphene and as a result make further steps easily progressable because of more easy dissolution of the functionalized graphene.

As unreacted graphite and graphene functionalized at its edges coexist in the freeze-dried products, such dried products are dissolved in solvent and graphene functionalized at its edge positions is centrifugally separated from the products so that the graphene is exfoliated.

The solvent changes depending on the type of organic material bonded at the edges of the graphene which are functionalized. The solvent is selected from the group consisting of water, methanol, ethanol, isoprophyl alcohol, toluene, benzene, hexane, heptane, m-cresol, ethyl acetate, carbon disulfide, dimethyl sulfoxide, dichloromethane, dichlorobenzene, chloroform, carbon tetrachloride, acetone, tetrahydrofuran, dimethylacetamide, N-methylpyrrolidone, dimethylformamide, acetic acid and mixtures thereof.

The centrifugal separation is performed at the rate of 1,000 rpm to 15,000 rpm, preferably of 7,000 rpm to 12,000 rpm, and for 30 sec to 20 minutes, preferably for 2 minutes to 15 minutes to exfoliate graphene functionalized at its edges.

When the rate of the centrifugal separation is less than 1,000 rpm, or the time of the centrifugal separation is less than 30 sec, the exfoliation is not accomplished. When the rate of the centrifugal separation is more than 15,000 rpm or the centrifugal separation is more than 20 minutes, there is a danger that the tube of a centrifugal separator would break.

The method of graphene fabrication according to the present invention includes reducing graphene functionalized at its edge positions according to the above method in air or in an inert atmosphere and removing organic material which functionalized at its edge positions.

An inert gas such as nitrogen, argon, helium, and neon gas can he used. The reduction is accomplished through the method of ultrasonic waves, the plasma, or the. heat treatment, etc, Reduction according to heat treatment, of the above reduction methods, is preferable. Heat treatment is carried out at temperatures of 300° C. to 1,200° C., and preferably 600° C. to 1,000° C., and for a time of 30 rains to 24 hours, and preferably 2 hours to 6 hours.

When the heat treatment temperature is more than 1,200° C. or the heat treatment time is more than 24 hours, there is a problem that the graphene etc., will get damaged. When the heat treatment temperature is less than 300° C. or the heat treatment time is less than 30 minutes, there is a problem that the organic material cannot be removed enough.

Pure graphene having a thickness of from about 0.3 to about 1,000 nm can be obtained by removing organic material from the graphene functionalized at its edge positions by reduction such as heat treatment.

The graphene obtained by removing the organic material has a purity that is 90% to 99%, preferably 95 to 99%, and more preferably 98% to 99%.

The graphene obtained by removing the organic material comprises a single layer or a plurality of layers and the thickness of the above layer is 0.3 nm to 1000 nm.

The present invention will now be described in detail through examples but the examples will be simply presented to understand the present invention without the intent to limit the scope of the present invention. The present invention will be defined within the scope of the claims set forth later.

EXAMPLE 1-1

Preparation of Graphene Functionalized at its Edges 5 g of graphite and 5 g of amino benzoic acid were added to 110 g of reaction medium comprising 100 g of methanesulfonic acid ($CH_3SO_3H$) and 10 g of phosphorus pentoxide ($P_2O_6$) from Sigma-Aldrich at a temperature of 100° C. for 72 hours. Or 5 g of graphite and 5 g of amino benzoic acid were added to 100 g of reaction medium comprising trifloromethanesulfonic acid ($CF_3SO_3H$) Sigma-Aldrich at a temperature of 100° C. for 72 hours. As a result, bonds of edge positions between graphene sheets were substituted by a covalent bond between the carbon at edge positions of the graphene and the carbonyl group of aminobenzoic acid, to functionalize edge positions of the graphene.

After that, the graphene functionalized at its edge positions was precipitated in water and it was again recovered and then treated for 3 days in water, and for 3 days in methanol by soxhlet and thereby unreactants such as methanesulfonic acid and phosphorus pentoxide, or trifluoromethanesulfonic acid, and amino benzoic acid were removed.

Thereafter, graphene functionalized at its edge positions, separated from the above unreactants was freeze-dried.

EXAMPLE 1-2

Preparation of Graphene Functionalized at Edge Positions 5 g of graphite and 5 g of 4-(2,4,6-trimethylphenoxy) benzamid were added to 110 g of reaction medium comprising 100 g of methanesulfonic acid(CH3SO3H) and 10 g of phosphorus pentoxide(P2O6) from Sigma-Aldrich at a temperature of 100° C. for 72 hours.

As a result, bonds of edge positions between graphene sheets were substituted by a covalent bond between the carbon at edge positions of graphene and the carbonyl group of 4-(2,4,6-trimethylphenoxy) benzamide, to functionalize edge positions of graphene.

After that, the graphene functionalized at its edge positions was precipitated in water. The precipitated graphene was again recovered and then treated for 3 days in water, and for 3 days in methanol by soxhlet and thereby reaction medium and unreactants such as unreacted 4-(2,4,6-trimethylphenoxy) benzamide were removed. Thereafter, graphene functionalized at its edge positions, separated from the above unreactants was freeze-dried.

EXAMPLE 2

Separation of Graphene Functionalized at Edge Positions 0.5 g of freeze-dried products obtained according to the above example 1-1 were dispersed in 500 ml of N-methyl pyrrolidone solvent and were agitated for 24 hours.

And then, dispersed freeze-dried products were centrifugally separated by a centrifugal separator at a rate of 10,000 rpm for 10 minutes to separate graphene functionalized at its edge positions from freeze-dried products.

Graphene functionalized at its edge positions, obtained by such separation had a width that is more than 2 micrometers and a length that is more than 10 micrometers.

Figure 3:
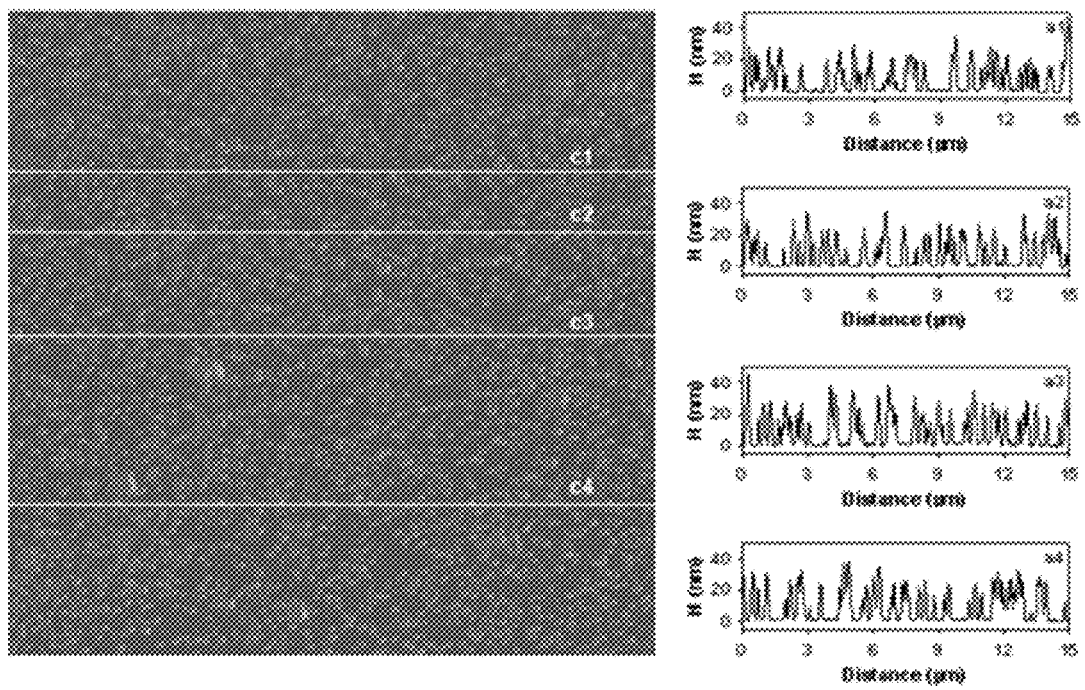
FIG. 3 shows experimental results which verify the width, the length and the thickness of graphene according to one example of the present invention.
Figure 4:
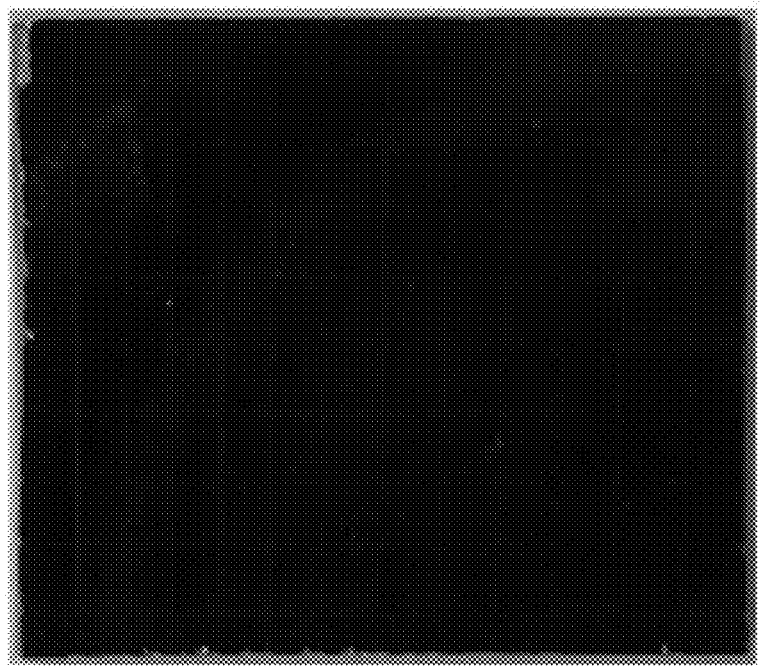
FIG. 4 is a film picture of a large sized graphene produced on a quartz plate according to one example of the present invention.

With regard to this, referring to FIG. 3, FIG. 3 shows the width and length both of the graphene. It can confirm that an exfoliated graphene has its width of more than 2 micrometers and its length of more than 10 micrometers and a molecular wedge type group is attached to out edge positions of graphene.

EXAMPLE 3

Production of High Purity Graphene

The heat treatment was carried out so as to remove organic material bonded at edge positions from graphene functionalized at edge positions which was obtained according to example 2, and to obtain high purity graphene.

In other words, high purity graphene was obtained by heat treating graphene functionalized at edge positions under a nitrogen or argon atmosphere at a temperature of 900° C. for about one hour, and removing organic material covalently bonded to edge positions of graphene. The high purity graphene formed at this time has a purity that is about 98.3% and a thickness that is from 0.8 to 5 nm (see FIG. 3).

Although the preferred examples of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for production of an edge-functionalized graphene comprising:
   providing graphite;
   reacting organic material having one or more functional groups with the graphite in a reaction medium comprising methanesulfonic acid and phosphorus pentoxide, or in a reaction medium comprising trifluoromethanesulfonic acid, thus to substitute force of edge positions between graphene sheets with covalent bonds between graphene and organic material,
   wherein the one or more functional groups include one or more selected from a group consisting of carboxylic acid group, amide group, sulfonic acid group, carbonyl chloride group and carbonyl bromide group, and
   wherein the organic material covalently attached to graphene acts as a wedge, and thereby exfoliating graphene functionalized at its edge positions.

2. The method according to claim 1, wherein the reaction medium comprising methanesulfonic acid and phosphorus pentoxide includes about 65 wt % to about 95 wt % of methanesulfonic acid and about 5 wt % to about 35 wt % of phosphorus pentoxide, based on the total weight of the reaction medium.

3. The method according to claim 1, wherein a remaining portion of the organic material except the one or more functional groups includes $C_1$-$C_5$ alkyl group, $C_2$-$C_5$ alkenyl group, $C_2$-$C_5$ alkynyl group, $C_3$-$C_{10}$ cycloalkyl group, $C_6$-$C_{15}$ aryl group, or $C_6$-$C_{15}$ aralkyl group, and the alkyl group, the alkenyl group, the alkynyl group, the cycloalkyl group, the aryl group, or the aralkyl group is unsubstituted, or substituted, wherein the substituent is selected from the group consisting of halo, nitro, amino, cyano, mercapto, hydroxyl, $C_1$-$C_4$ alkyl, $C_1$-$C_4$ alkoxy, formyl, $C_1$-$C_4$ alkylcarbonyl, phenyl, benzoyl, phenoxy and the combination thereof.

4. The method according to claim 1, wherein the organic material is benzoic acid which is unsubstituted or substituted, wherein the substituent is selected from the group consisting of halo, nitro, amino, cyano, mercapto, hydroxyl, $C_1$-$C_4$ alkyl, $C_1$-$C_4$alkoxy, formyl, $C_1$-$C_4$alkylcarbonyl, phenyl, benzoyl, phenoxy and the combination thereof.

5. The method according to claim 1, wherein the organic material is any one selected from the group consisting of 3-aminobenzoic acid, 4-aminobenzoic acid, 4-(4-aminophenyl)benzoic acid, 4-(3-aminophenyl)benzoic acid, 5-aminoisophthalic acid, 4-(4-aminophenoxy)benzoic acid, 4-(3-aminophenoxy)benzoic acid, 3,4-diaminobenzoic acid, 3,5-diaminobenzoic acid, 2-phenoxybenzoic acid, 3-phenoxybenzoic acid, 4-phenoxybenzoic acid, 3,5-diphenoxybenzoic acid, 5-phenoxyisophthalic acid, 4-phenyl-(4-phenoxy benzoic acid), 4-phenoxy-(4-phenylbenzoic acid), 4-ethylbenzoic acid, 2-ethylbenzoic acid and 4-ethylphenoxybenzoic acid.

6. The method according to claim 1, further comprising:
   dispersing graphene functionalized at its edge positions in solvent, and
   centrifugally separating the graphene from graphite.

7. The method according to claim 6, further comprising:
   reducing graphene functionalized at its edge positions in air or an inert atmosphere,
   and removing organic material which functionalized at edges of graphene.

8. The method according to claim 7, wherein the reduction is a heat treatment.

9. The method according to claim 8, wherein the heat treatment is performed at a temperature of about 300° C. to about 1,200° C. for about 30 minutes to about 24 hours.

10. The method according to claim 7, wherein graphene obtained after removing the organic material has a purity that is about 90% to about 99%.

11. The method according to claim 7, wherein graphene obtained after removing the organic material comprises one layer or a plurality of layers and has a thickness that is about 0.3 nm to about 1000 nm.

* * * * *